United States Patent [19]
Friedman et al.

[11] 3,932,622
[45] Jan. 13, 1976

[54] SKIN MOISTURIZER

[75] Inventors: Herman H. Friedman, Bayside; Linda K. Halik, Ossining, both of N.Y.; Milton H. Schwarz, Westport, Conn.

[73] Assignee: General Foods Corporation, White Plains, N.Y.

[22] Filed: Jan. 11, 1974

[21] Appl. No.: 432,722

[52] U.S. Cl. ............... 424/168; 424/172; 424/319; 424/358
[51] Int. Cl.² ............... A61K 31/195; A61K 31/00; A61K 7/00
[58] Field of Search ............ 424/172, 319, 65, 172, 424/168; 260/534 G, 529

[56] References Cited
UNITED STATES PATENTS

| | | | |
|---|---|---|---|
| 3,016,334 | 1/1962 | Lewis | 424/319 |
| 3,235,457 | 2/1966 | Deerfield | 424/65 |
| 3,274,063 | 9/1966 | Nieper et al. | 424/319 |

FOREIGN PATENTS OR APPLICATIONS

| | | |
|---|---|---|
| 1,153,408 | 5/1969 | United Kingdom |
| 1,485,602 | 5/1967 | France |

OTHER PUBLICATIONS

American Perfume & Cosmetics, Vol. 82, Apr. 1967, pp. 47–48, 50, 52, 54, 56, 58.
Chemical Abstracts, Vol. 79: 57576c; Vol. 79: 96838j; Vol. 74: 91169d; Vol. 71: 42173e; Vol. 67: 5645g & Vol. 66: 118776y.
Chemical Abstracts–Jan.–June 1973, Formula Index, p. 327F.

*Primary Examiner*—Donald B. Moyer
*Attorney, Agent, or Firm*—Thaddius J. Carvis; Daniel J. Donovan; Bruno P. Struzzi

[57] ABSTRACT

Disclosed is a skin moisturizing composition capable of providing a super-moisturizing effect over extended periods of time. The composition comprises a water-in-oil emulsion containing an amount of a di-alkali metal salt of N-acetyl glutamic acid which is effective to provide a super-moisturizing effect when applied to the skin.

9 Claims, No Drawings

SKIN MOISTURIZER

BACKGROUND OF THE INVENTION

The present invention relates to skin moisturization, and more specifically, to a composition having a super-moisturing effect on the skin.

Physiologically, the skin is composed of an external integument called the stratum corneum, an underlying basal layer and the dermis. This entire skin organ functions as a primary moisture reservoir for the body.

The stratum corneum, which varies in thickness from approximately 15 microns on the face and the backs of the hands to 500 microns on the soles of the feet and the palms of the hands, plays a significant role in controlling the level of moisture in the skin. It is composed of keratinized cells, a natural moisturizing factor and lipids. All of these function together as a protective coating, as well as a moisture barrier to retain moisture within the skin.

In the basal area, which lies below the stratum corneum, the cells of the skin undergo change from normal cell structure to the keratinized layer of the corneum. During this change, protein breakdown products are formed, among which are pyrroledone carboxylic acids, which function as natural moisturizing compounds. Below the basal layer, lies the normal dermis of the skin, which holds and transports water to the area.

Water is extremely important to the proper physical condition and appearance of skin. Dry and chapped skin is largely the result of an insufficient level of moisture in the stratum corneum. Soft, pliable, healthy skin cannot be maintained in the absence of the proper level of moisture in the stratum corneum.

The level of moisture in the skin is dependent upon a number of factors. Among these are the water binding potential of the stratum corneum, the rate at which water is supplied to the internal layers of the stratum corneum, and the rate at which water is lost from the external surface of the skin. With these factors in mind, investigators have, for a number of years, been actively searching for ways to maintain proper levels of moisture in the skin.

Because emulsions contain two media, water and oil, thought to be important in skin moisturization, they have been widely used in formulating moisturizing compositions. Oil-in-water emulsions have received the most attention principally because until recently they were much better understood than water-in-oil emulsions. Thus, they were generally easier to prepare and gave better stability. In order to increase their moisturizing effectiveness, many workers have added humectants to these emulsions.

Desirably, a humectant for use in moisturizing cosmetic preparations should have the ability to super-moisturize the skin over extended periods of time. While the ability to prevent drying of the preparation itself may be important for aesthetic ressons as they may relate to consumer acceptance, the presence of this property in a preparation does not establish the effectiveness of the preparation as a skin moisturizer. The essential feature is whether or not the skin is moisturized. A beneficial side effect may be that the preparation itself does not dry out.

Typical of the humectants used in early work are glycerin, the polyethylene glycols, and gums. These humectants will decrease the rate of water loss from the vehicle itself and prevent crust formation in oil-in-water emulsions. However, it is reported that these compounds neither decrease the rate of water loss from, nor increase the water content of, the stratum corneum. (Shelmire Jr., J. B.; Archives Of Dermatology; 82:24-31; 1960). Shelmire asserts, in fact, that while the vehicles containing these humectant substances will themselves dry out less rapidly, they actually result in the formation of a less efficient water-retaining film than those preparations excluding them.

Thus, the early workers, believing that humectants were important, apparently overlooked an important fact–how the humectant affected the moisture level of the skin.

A later worker (Laden, U.S. Pat. No. 3,235,457) discloses certain humectants which are said to maintain a soft, smooth feeling in the skin. Among the compounds disclosed by Laden are the sodium, potassium and ammonium salts of 2-pyrrolidone-5-carboxylic acid, 1-methyl-2-pyrrolidone-5-carboxylic acid, 2-pyrrolidone-4-methyl-5-carboxylic acid, N-acetyl glycine, L-acetamido butyric acid, and N-acetyl alanine. Laden discloses that for cosmetic preparations, it is possible to employ the free carboxylic acids because the free acid will react with sodium ions naturally present on the skin or in perspiration to form the sodium salt while in place on the skin. These compounds are, however, quite costly; and, suitable alternatives and even more effective compounds would be desired.

SUMMARY OF THE INVENTION

It is an object of the present invention to provide a moisturizing cosmetic composition which will provide a super-moisturizing effect when applied to the skin.

It is a further object of the present invention to provide a moisturizing cosmetic composition which will provide a super-moisturizing effect over extended periods of time when applied to the skin.

These and other objects are accomplished according to the present invention which provides a moisturizing cosmetic composition comprising a water-in-oil emulsion and an amount of a di-alkali metal salt of N-acetyl-glutamic acid which is effective to provide a super-moisturizing effect when the composition is applied to the skin.

DETAILED DESCRIPTION

The present invention is based upon the discovery that the di-alkali metal salts of N-acetylglutamic acid, when employed in water-in-oil emulsions, provide a super-moisturing effect on skin. This narrowly defined group of salts of this specific amino acid derivative are particularly effective, when applied to the skin in water-in-oil emulsions, in increasing the moisture level of the skin not only initially, but further, over extended periods of time. It is presently believed that the unique ability of these compounds to bind water is due to their electronic configuration when ionized.

The N-acetylglutamic acid is commercially available, and can be purchased in the requisite purity for cosmetic use. Caution should be taken, however, to assure suitable purity. If further purification is required, this can be accomplished in known manner. Alternatively, the N-acetylglutamic acid can be prepared immediately prior to use. For example, it can be prepared by acetylating glutamic acid in aqueous solution with acetic anhydride. The resulting N-acetylglutamic acid, in the form of white crystals is then purified in known manner.

Any of the di-alkali metal salts of N-acetylglutamic acid which are suitable for cosmetic use can be employed according to the present invention. The sodium and potassium salts, especially the potassium salts, are preferred. These salts can be easily prepared by neutralizing the acid with any suitable base containing the appropriate alkali metal cations. For example, the disodium salt can be prepared by neutralizing N-acetyl-L-glutamic acid with a slight excess of sodium hydroxide, and the dipotassium salt with a slight excess of potassium hydroxide.

These salts are employed in the cosmetic composition in any amount which is effective to super-moisturize the skin. Typically, these di-alkali metal salts will be employed in amounts greater than about 1% by weight of the emulsion. Preferably, they are employed in an amount of from about 2% to about 5%, and more preferably, from about 2.5% to about 3.5% by weight of the emulsion. It would, of course, be possible to employ a combination of these salts in a combined amount effective to super-moisturize the skin.

In addition to the di-alkali metal salts of N-acetylglutamic acid, the moisturizing cosmetic composition according to the present invention essentially includes a water-in-oil emulsion. The use of the water-in-oil emulsion is believed necessary to obtain a significant moisturizing effect. This emulsion should contain a ratio of water-to-oil of from between about 1:20 to about 20:1. Preferably the water-to-oil ratio will be within the range of from about 1:2 to about 3:1, and more preferably from about 1:1 to about 2:1. The selection of the exact water-in-oil ratio and the emulsifier system employed will depend upon the type of product desired, e.g. whether it is to be a lotion or a cream and what the viscosity and feel should be. An added advantage of the present invention is that the water-in-oil emulsions prepared in accordance with the teachings herein are less viscous, greasy, or oily in feel than otherwise and are, therefore, more suitable for cosmetic use.

It is usually necessary to employ at least one emulsifier capable, alone or in combination with other emulsifiers, of producing a shelf-stable water-in-oil emulsion. Typical of the emulsifiers which can be employed are beeswax/borax, lime water/stearic acid, sorbitan trioleate, sorbitan sesquioliate, oleth-2, and cholesterol absorption base. A preferred emulsifier system comprises beeswax/borax and lime water/stearic acid at a level of about 4% by weight of the emulsion. These and other emulsifiers can be employed at any level effective to form a suitably stable emulsion. The exact levels are easily determined by knowledge within the skill of the art.

The oil phase of the emulsion will typically comprise known oils acceptable for cosmetic use, among which are the animal, vegetable, and mineral oils. With these, also in the oil phase, a number of other compounds can be employed to modify the texture, feel, rub-in, afterfeel, viscosity, and other physical attributes of the product. For example, waxes can be added to increase texture, and lanolin emulsifiers can be added to modify product texture and skin feel. Further, such materials as lanolin alcohols can be added for their known special textural and tactile effects on the skin.

The water phase of the emulsion contains the water and the water soluble components of the composition. Preferably, the water is employed as saturated lime water and calcium chloride is added to assure satisfactory stability to the water-in-oil emulsion. Also present in the water phase may be water soluble or dispersible materials which can be added for the purpose of adjusting the physical properties of the emulsion during processing or in final form.

In preparing the emulsion, the oil and the water phases are both prepared separately and then combined with vigorous agitation to effect emulsification. The oil phase can be prepared in known manner, such as melting and blending the ingredients to form a uniform phase. The water phase is also prepared in known manner, such as simply mixing until all of the soluble materials are dissolved. The oil and water phases are admixed and blended in the liquid state. Thus, for example, the oil phase may be at a higher temperature than the water phase. Vigorous mixing in a device such as a Lightnin mixer will provide adequate agitation for emulsification. The product should be cooled after preparation. Fragrances, such as in the form of Perfume oil, can be added after emulsification, if desired, to prevent volatilization. The N-acetyl-L-glutamic acid can be added to the oil phase and then neutralized with the alkalin in the water phase when mixed or preferably it can be dissolved as the di-alkali metal salt prior to emulsification.

The following examples are presented for the sole purpose of further illustrating and explaining the present invention and are not to be taken as limiting in any sense. Unless otherwise specified, all parts and percentages are by weight.

EXAMPLE I

Two moisturizing cosmetic lotion bases were prepared having the compositions shown in Table I.

TABLE I

| Ingredients | Parts By Wt. In Samples | |
| --- | --- | --- |
| | A | B |
| Oil Phase | | |
| Amerchol L-101 lanolin alcohols extract | 1.8 | 1.8 |
| Oleinate 288 glycerol trioleate | 0.9 | 0.9 |
| Stearic acid | 1.5 | 1.5 |
| White perfecta petrolatum | 5.0 | 5.0 |
| Cosmetic fluid No. 687 petroleum distillate | 15.3 | 15.3 |
| Arlacel No. 83 sorbitan sesquioleate | 2.7 | 2.7 |
| Standamul G 2-octa dodecanol | 1.5 | 1.5 |
| Peach kernel oil | 0.5 | 0.5 |
| Standamul 1414E myristyl ethoxy myristate | 3.4 | 3.4 |
| Bees' wax | 2.0 | 2.0 |
| Ceraphyl 230 diisopropyl adipate | 1.8 | 1.8 |
| Ceraphyl 375 isostearyl neopentonate | 7.0 | 7.0 |
| Ceraphyl 368 2-ethyl hexyl palimitate | 9.0 | 9.0 |
| Water Phase | | |
| N-acetyl-L-glutamic acid | 3.0 | 0 |

TABLE I-continued

| Ingredients | Parts By Wt. In Samples | |
|---|---|---|
| | A | B |
| Lime water (Sat'd) | 45.5 | 45.5 |
| Ca Cl$_2$ | 0.17 | 0.17 |
| Distilled water | 1.7 | 1.7 |
| KOH | 2.07 | 2.07 |
| Sodium borate (borax) | 0.07 | 0.07 |
| Methyl Paraben methyl parahydroxy benzoate | 0.1 | 0.1 |
| Propyl Paraben propyl parahydroxy benzoate | 0.01 | 0.01 |

Included in the water phase of separate 100 gram portions of base formulation A was the indicated amount of N-acetyl-L-glutamic acid and sufficient KOH to form the dipotassium salt thereof.

The moisturizing cosmetic lotion bases of the above formulations were prepared as follows:

1. A suitable quantity of saturated lime water was prepared by dissolving 3 grams of calcium hydroxide in each 1,000 grams of distilled water. The resulting suspension was stirred for a few minutes and allowed to cool to and stand at 10°C for a minimum time of 24 hours. At the end of the cooling period, the mixture was filtered and the filtrate returned to the refrigerator where stored until used.

2. All of the oil phase ingredients were weighed into a suitable jacketed kettle, fitted with a tilt-away, counter-roating scraper-agitator. The scraper-agitator was tilted up and out of the way and a low rpm Lightnin stirrer fitted with an 8 inch - 4 blade-satellite ring propeller was installed. The resulting oil phase mixture was covered and heated to 90°C.

3. The water phase was prepared by weighing lime water (saturated, filtered and at 10°C) into a jacketed kettle fitted with a Lightnin stirrer. All water phase ingredients were then added and the Lightnin stirrer was started to give a rapid vortexless turnover. Stirring was continued while maintaining a 10°C temperature until the solution became almost clear after a short period of time.

4. The water phase was then added to the oil phase in the following manner: With the oil phase at 90°C, the Lightnin agitator was started and a good vortex obtained. Addition of the 10°C water phase was started at this time. The water was poured at moderate speed until all of the lime water was added. At this juncture, the crude emulsion started to thicken quite drastically; the Lightnin agitator was removed and the counter-roating scraper was lowered. The scraper was operated at sufficient rpm to maintain efficient product turnover.

5. After 10 to 15 minutes scraper operation, cooling the moisturizing base with tap water through the jacket of the kettle was begun. Cooling was continued to a termperature of from about 22°C to 25°C.

These moisturizing cosmetic bases were then prepared as lotions using tritiated water and tested for the moisturizing effectiveness of the lotions, employing the following procedure:

a. A 5.0 gram aliquot of each formulation was accurately weighed into a tared beaker.

b. The beaker containing the aliquot was placed in an 80°C water bath for 2-3 minutes.

c. a 0.5 gram aliquot of tritiated water (specific activity; 1 millicurie/gram) was weighed into the formulation. The mixture was hand stirred to room temperature. These samples were tested on rabbits and were prepared on the day prior to initial application to the rabbit skin sites. Aliquots (0.1 ml) were counted on the last day of use in the rabbit skin studies. The measured radioactivity content of 0.1 ml of the formulations was approximately $3 \times 10^6$ counts/minute.

d. The abdominal fur of the test rabbits was removed with electric clippers approximately 18 hours prior to application of the test formulations.

e. On the morning of the test, each test animal was restrained on a rabbit-board and the experimental skin sites were examined to determine the acceptability of the shaving and the absence of skin abrasions.

f. Circular (2.5 cm diameter) spots were then drawn on the shaved abdominal area of each rabbit.

g. One-tenth milliliter of each formulation was placed in the center of the designated spot and massaged gently into the skin for one minute. Each aliquot of assigned formulation was placed on the designated skin site using this procedure.

h. Restraint of the animal was maintained for four hours to permit penetration of the formulation at which time each treated skin site was rinsed with water and patted dry.

i. The rabbits were sacrificed and the abdominal skin was removed, placed on a cardboard and put in a dry-ice freezer for 10 minutes. Using a sharp cork-bore (½ inch I.D.), skin sections were cut from the center of the treated skin sites, placed in pre-marked vials and returned to the dry-ice freezer.

j. Frozen sections (50 microns in thickness) were obtained using a freezing microtome. The epidermis was brought to the blade last to avoid contamination of the underlying sections with any surface residue to radioactivity. Each section was collected on a thin filter-paper segment.

k. Two skin sections were dropped into each scintillation vial, to which 15 milliters of a methanal/dioxane counting solution were added. The vials were then chilled for 10 minutes and counted for 1 minute.

l. Tritium counts are made in this manner at intervals of 2 hours and 4 hours. Results are expressed as corrected counts per minute for each 100 microns of skin thickness (0–100, 100–200, 200–300, 300–400 and 400–500). For each formulation, averages are obtained from four different skin sites, one site from each of 4 rabbits.

NOTE: Rabbits are known to differ in their response to the same treatment, and since one rabbit can only receive four treatments, when there are more than four treatments, a statistical design that allows for this is employed. The design used here is known as a Balanced Incomplete Block and provides for adjusting the observed treatment averages for differences in rabbits. The procedure is outlined on Pages 68–72 of Volume III of the Design Of Experiments Course written by Dr. J. Stuart Hunter and published in 1968 by Westinghouse Learning Press.

The results are summarized in Table II.

TABLE II

| SAMPLE | COUNTS | |
|---|---|---|
| | 2 HOURS | 4 HOURS |
| A | 9761 | 9604 |
| B | 5520 | 6037 |

EXAMPLE II

A moisturizing cosmetic lotion base was prepared having the composition set forth in Table III.

TABLE III

| Ingredient | Wt.% |
|---|---|
| Oil Phase | |
| Carnation mineral oil | 19.4 |
| White perfecta petrolatum | 5.0 |
| Amerchol L-101 lanolin alcohols extract | 5.0 |
| OHlan hydroxylated lanolin | 3.0 |
| Arlacel 83 sorbitan sesquioleate | 3.0 |
| Oleinate 288 glycerol trioleate | 3.0 |
| Ceraphyl 140 decyl oleate | 3.0 |
| Sweet almond oil | 2.0 |
| Stearic acid | 1.5 |
| Amerlate P isopropyl lanolate | 1.0 |
| Ceraphyl 424 myristyl myristate | 0.1 |
| Water Phase | |
| Lime water (saturated) | 50.0 |
| Ca Cl$_2$ | 0.48 |
| Distilled water | QS |
| | 100.0% |

To the oil phase of separate 100 gram portions of this base formulation was added 3 grams of N-acetyl-L-glutamic acid, and to the water phase a. 1.03 grams of KOH to prepare the monopotassium salt of the N-acetyl-L-glutamic acid; and
b. 2.06 grams of KOH to prepare the dipotassium salt of the N-acetyl-L-glutamic acid.

Two cosmetic lotion compositions of the above formulation containing the
(a) monopotassium salt of N-acetyl-L-glutamic acid; and
(b) the dipotassium N-acetyl-L-glutamic acid were prepared as according to the procedure Example I except that:
(a) the N-acetyl-L-glutamic acid was added with slow stirring to the oil phase which had been preheated to 80°C; and
(b) the oil phase was stirred slowly to 42°C and the water phase at 10° was slowly added with stirring; and
(c) the emulsion was stirred for five minutes at room temperature and for ten minutes in an ice water bath.

Both of these samples were tested for moisturization in the manner outlined in Example I, but this time tritium counts were made at intervals of ½ hour, 1 hour, 2 hours, 4 hours, and 8 hours. The results are summarized in Table IV.

TABLE IV

| SAMPLE | COUNTS | | | | |
|---|---|---|---|---|---|
| | ½ hr. | 1 hr. | 2 hrs. | 4 hrs. | 8 hrs. |
| Mono-Potassium Salt | 23516 | 21243 | 5254 | 474 | 154 |
| Di-Potassium Salt | 29498 | 24087 | 23652 | 21749 | 9974 |

While the above examples and explanation are presented for the purpose of describing the invention, many modifications and variations thereof will become apparent to those skilled in the art upon reading the above disclosure. It is intended that all such modifications and variations be included within the scope of the invention which is defined by the scope of the following claims.

What is claimed is:

1. A moisturizing cosmetic composition which comprises a stable water-in-oil emulsion and an amount of a di-sodium or di-potassium salt of N-acetylglutamic acid which is effective to provide a super-moisturizing effect when applied to the skin.

2. A moisturizing cosmetic composition according to claim 1 wherein the alkali metal is potassium.

3. A moisturizing cosmetic composition according to claim 1 which further comprises as an emulsifier lime water and stearic acid.

4. A moisturizing cosmetic composition according to claim 1 wherein the dipotassium salt of N-acetylglutamic acid is present in an amount of greater than 1 percent by weight of the composition.

5. A moisturizing cosmetic composition according to claim 4 wherein the dipotassium salt of N-acetylglutamic acid is present in an amount of from about 2% to about 5% by weight of the composition.

6. A moisturizing cosmetic composition according to claim 5 wherein the water is present in the emulsion at a water-to-oil ratio of from about 1:2 to about 3:1.

7. A moisturizing cosmetic composition according to claim 6 which further includes as an emulsifier lime water and stearic acid.

8. A moisturizing cosmetic composition according to claim 7 wherein the dipotassium salt of N-acetylglutamic acid is present in an amount of from about 2.5% to about 3.5% by weight of the composition.

9. A moisturizing cosmetic composition according to claim 8 wherein the water is present in the emulsion at a water-to-oil ratio of from about 1:1 to about 2:1, and which further comprises as an emulsifier for the combination of beeswax and borax.

* * * * *

Disclaimer and Dedication 3,932,622.—*Herman H. Friedman*, Bayside, *Linda K. Halik*, Ossining, N.Y., and *Milton H. Schwarz*, Westport, Conn. SKIN MOISTURIZER. Patent dated Jan. 13, 1976. Disclaimer and Dedication filed Mar. 31, 1976, by the assignee, *General Foods Corporation*.

Hereby disclaims and dedicates the entire term of said patent to the public.
[*Official Gazette May 25, 1976.*]